United States Patent [19]

Bair

[11] Patent Number: 5,988,168
[45] Date of Patent: Nov. 23, 1999

[54] METHOD AND APPARATUS FOR ESTABLISHING A SURGICAL AIRWAY

[76] Inventor: Aaron E. Bair, 215 Diablo Ave., Davis, Calif. 95616

[21] Appl. No.: 08/857,911

[22] Filed: May 16, 1997

[51] Int. Cl.⁶ .................................................. A61M 16/00
[52] U.S. Cl. ...................................... 128/207.29; 606/172
[58] Field of Search ...................... 128/207.29; 606/170, 606/172, 174; 604/117; D8/57; 30/146

[56] References Cited

U.S. PATENT DOCUMENTS

| | | |
|---|---|---|
| 241,036 | 5/1881 | Lyman . |
| D. 310,714 | 9/1990 | Dolwick .................................. D24/10 |
| 2,725,629 | 12/1955 | Jodhunter . |
| 2,834,349 | 5/1958 | Springer . |
| 2,873,742 | 2/1959 | Shelden . |
| 2,991,787 | 7/1961 | Shelden et al. . |
| 3,759,263 | 9/1973 | Taylor . |
| 3,893,454 | 7/1975 | Hagelin . |
| 4,182,337 | 1/1980 | Nickson . |
| 4,285,344 | 8/1981 | Marshall . |
| 4,608,982 | 9/1986 | Pollard . |
| 4,889,112 | 12/1989 | Schachner et al. . |
| 5,147,356 | 9/1992 | Bhatta ..................................... 606/174 |
| 5,217,007 | 6/1993 | Ciaglia . |
| 5,219,354 | 6/1993 | Choudhury et al. ..................... 606/174 |
| 5,279,285 | 1/1994 | Griggs . |

FOREIGN PATENT DOCUMENTS

WO 91/08709  6/1991  WIPO .

OTHER PUBLICATIONS

Brofeldt et al., "An Easy Cricothyrotomy Approach: The Rapid Four–Step Technique," Academic Emergency Medicine, vol. 3, No. 11, pp. 1060–1063, Nov. 1996.

Milner et al., "Review Article Emergency Criothyrotomy," Journal of Laryngology and Otology, vol. 105, pp. 883–885, Nov. 1991.

Johnson et al., "Cricothyrotomy Performed by Prehosptal Personnel: A Comparison of Two Techniques in a Human Cadaver Model," American Journal of Emergency Medicine, vol. 11, No. 3, pp. 207–209, May 1993.

Ravlo et al., "A Comparison Between Two Emergency Cricothyroidotomy Instruments," ACLA Anaesthesiol Scand, vol. 31, pp. 317–319, 1987.

Weiss, S., "A New Emergency Cricothyroidotomy Instrument," The Journal of Trauma, vol. 23, No. 2, pp. 155–158, Feb. 1983.

*Primary Examiner*—Aaron J. Lewis
*Attorney, Agent, or Firm*—John P. O'Banion

[57] ABSTRACT

An apparatus and method for performing emergency cricothyrotomy on a patient. The apparatus includes a pair of handles with an arcuate tip connected to the distal end of each handle with both sets of handles/tips attached together by a detachable pivot mechanism. The handles are angled away opposite in direction to the arcuate tips. The arcuate tips can grip a surgical scalpel which has at least one hub protruding from the side of the scalpel thereby limiting the incision depth to which the scalpel can cut. The arcuate tips are held apart by a spring mechanism but can be locked together. When used during a cricothyrotomy procedure, the apparatus engages a scalpel which is conjunctively used to make an incision into the patient's the skin and cricothyroid membrane. Once entry into the patient's airway is accomplished, the scalpel is removed. The arcuate tips are rotated and spread apart, thus allowing a tracheal tube to be inserted into the airway between the arcuate tips. The arcuate tips are then removed from the airway by angling the handles downward.

14 Claims, 8 Drawing Sheets

FIG. — 2

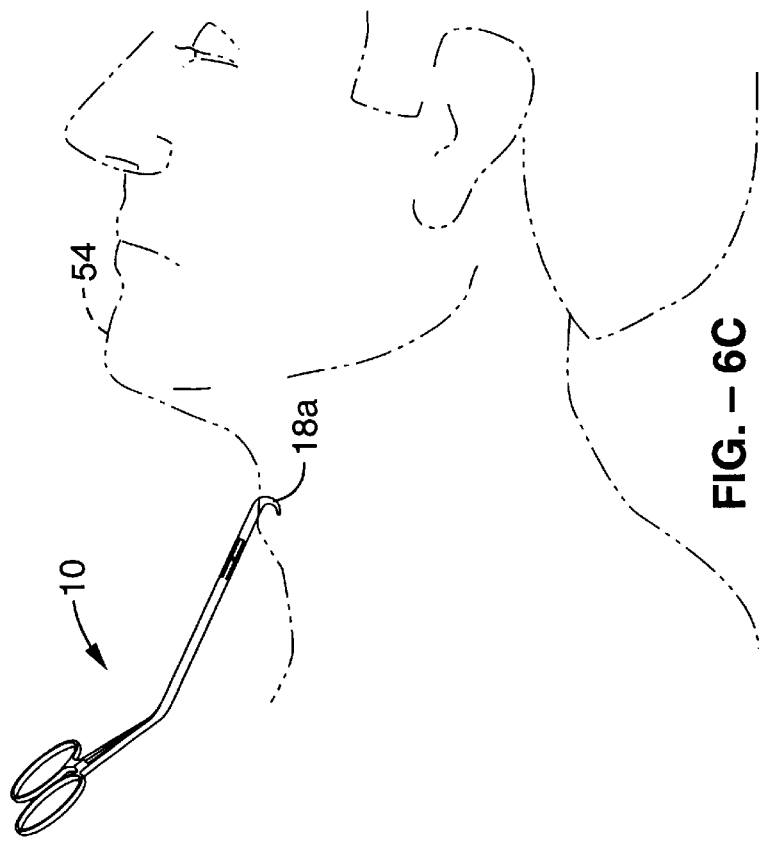
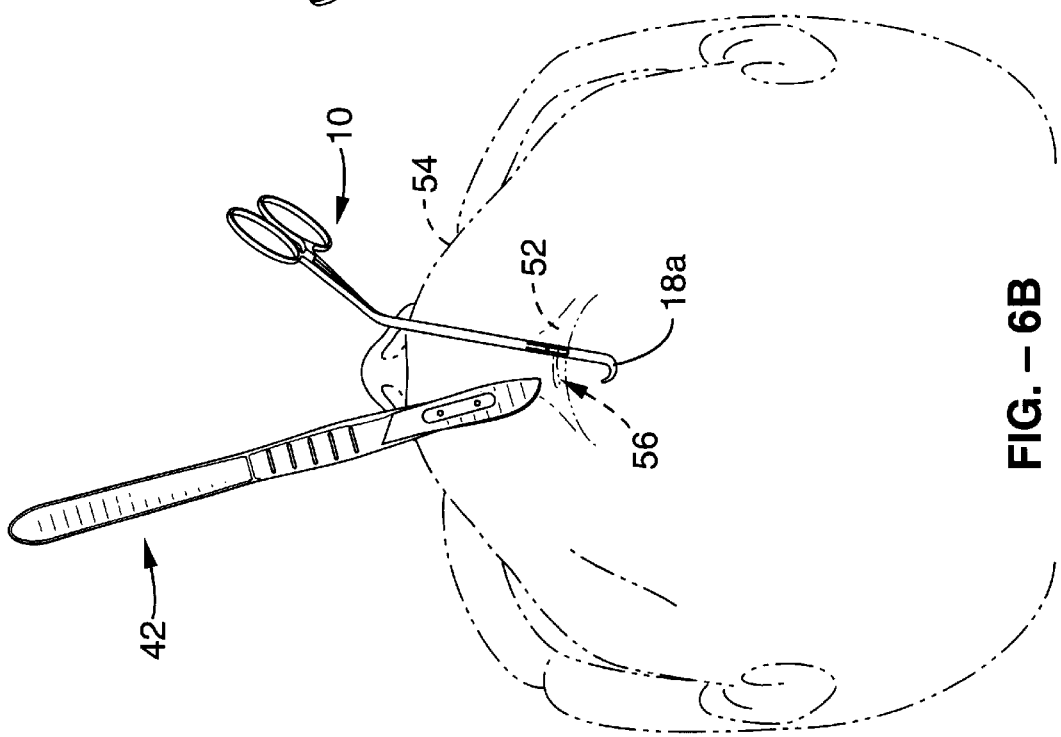
FIG. – 6C
FIG. – 6B

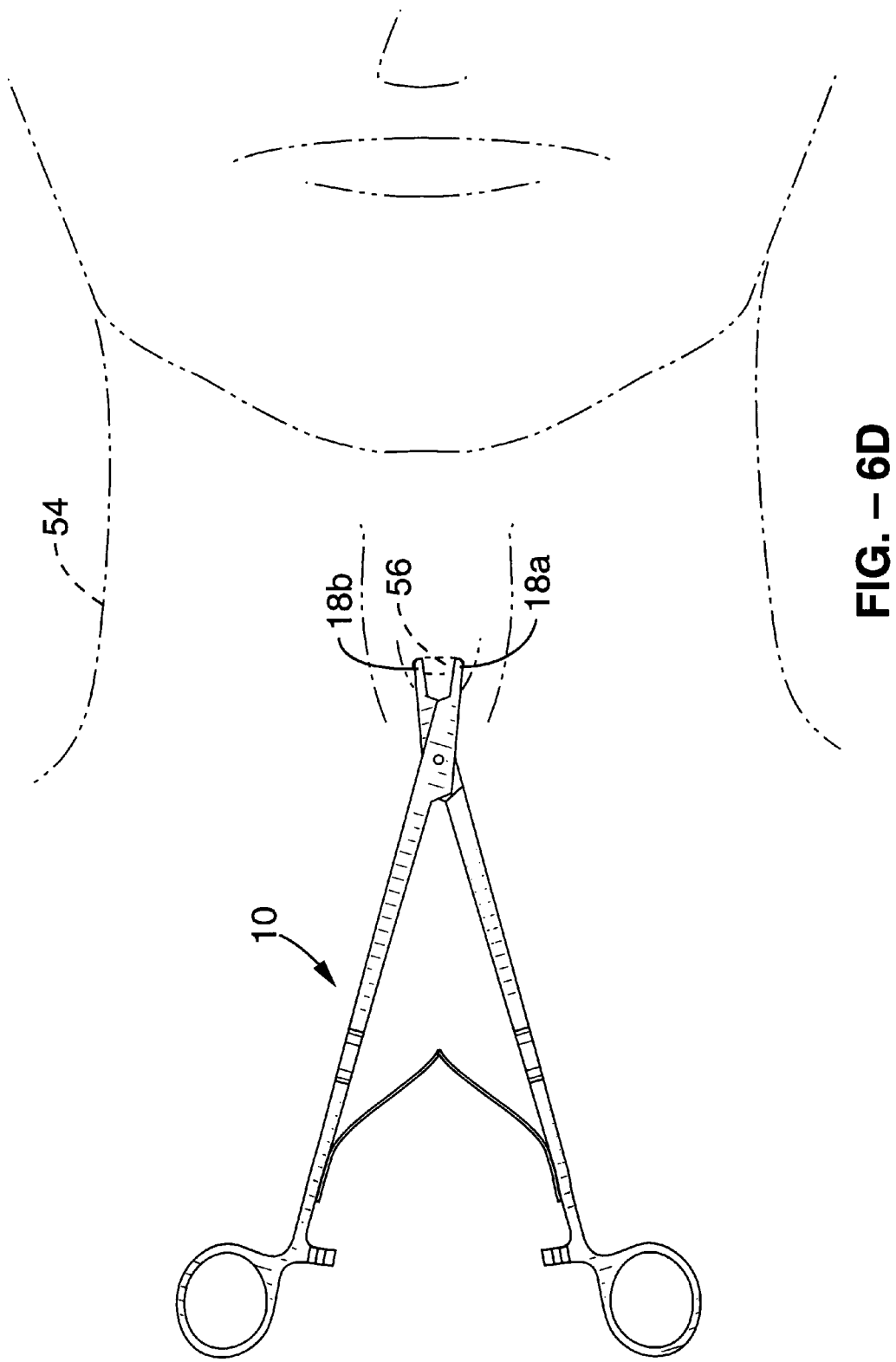

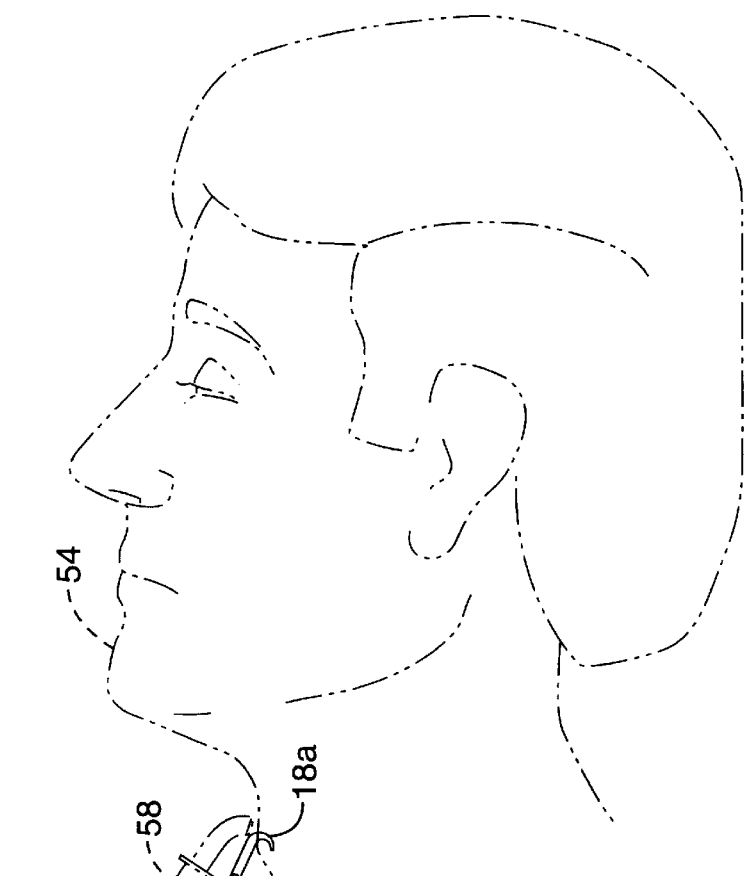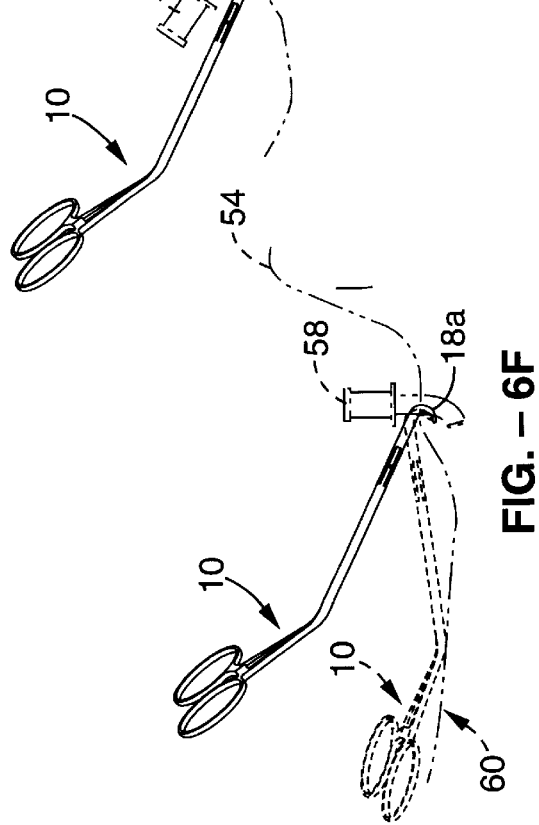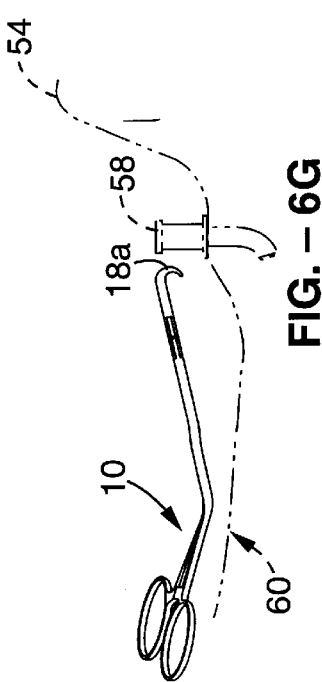

5,988,168

METHOD AND APPARATUS FOR ESTABLISHING A SURGICAL AIRWAY

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Field of the Invention

This invention pertains generally to instruments and techniques for establishing surgical airways, and more particularly to a method and apparatus for emergency surgical cricothyrotomy.

2. Description of the Background Art

During medical emergencies, there is an important need to access and control the patient's airway. A lack of oxygen to the patient, even for a brief period of time, may prove fatal. Patients who are inflicted with upper airway obstructions generally receive a surgical airway when non-invasive techniques fail to clear their upper airway. There are generally three common approaches to creating a surgical airway: needle tracheotomy, standard tracheotomy, and cricothyroidotomy (also known as cricothyrotomy).

Needle tracheotomy involves insertion of a large-bore needle into the patient's trachea to allow the patient to breathe. This procedure is, for the most part, unrealistic because the largest commonly available needle in the hospital setting is approximately fourteen gauge. This small size generally fails to provide adequate airflow capacity to a patient suffering from trauma.

Standard tracheotomy involves making two incisions, one immediately following the other, which must penetrate into the trachea. This often results in excessive bleeding and thus is a disfavored approach.

Cricothyrotomy has replaced the foregoing crude procedures to create an airway in the patient's trachea. Cricothyrotomy became established as the preferred method of surgical emergency management during the 1970s and early 1980s. It is easier to learn, quicker to perform, and is overall a safer procedure for the emergency medical physician who performs surgical airways very infrequently. Cricothyrotomy is performed by creating an opening in the cricothyroid membrane. The airway lies anterior to the esophagus and the cervical spine and is usually located in the midline of the neck. The surface anatomy of the neck is easily recognizable; in the anterior part of the neck, the anatomic landmarks include the hyoid bone, the thyroid cartilage, the cricoid cartilage, and the tracheal rings.

The general procedure for surgical cricothyrotomy is as follows: (1) locate the cricothyroid membrane; (2) make a vertical skin incision over the cricothyroid membrane; (3) stabilize the larynx with a tracheal hook while an incision is made in the cricothyroid membrane; (4) enlarge the incision in the cricothyroid membrane using hemostats or the blunt end of a scalpel; and (5) insert a tracheotomy tube between the curved hemostats. This surgical procedure requires, at minimum, the following tools: (1) a scalpel for making the incision; (2) a tracheal hook to stabilize the larynx; (3) a hemostat or second scalpel to enlarge or dilate the incision in the cricothyroid membrane; and (4) a tracheotomy tube to allow passage of air into the airway.

Because a surgical cricothyrotomy is done during an emergency where there is little or no preparation time available, there exists a need to minimize the number of instruments required by the emergency room physician and simplify the procedures involved, thus increasing the probability of saving the patient's life. The present invention satisfies those needs, as well as others, and overcomes the deficiencies inherent in coventional techniques and instruments.

BRIEF SUMMARY OF THE INVENTION

The present invention pertains to a surgical instrument and procedure for performing an emergency surgical cricothyrotomy using that instrument.

By way of example, and not of limitation, the apparatus of the invention generally comprises a pair of arcuate hooks operatively coupled to a pair of handles by elongated shafts. The shafts are pivotally coupled to provide a scissor-like action, and the handles are angularly offset in relation to the axis of the shafts in a direction opposite to the direction of curvature of the hooks. The blade of a scalpel can be placed between and held in position by the hooks when the handles are closed together. Hubs placed on the sides of the scalpel adjacent the blade will abut the inner radius of the hooks so as to limit protrusion of the blade beyond the hooks. In this way, the scalpel can be used to make an incision, but the incision depth is limited by the amount of blade protrusion.

To perform a cricothyrotomy, the apparatus engages a scalpel and the assembly is conjunctively used to make an incision into the patient's the skin and cricothyroid membrane. Once entry into the patient's airway is accomplished, the scalpel is removed. The arcuate hooks are then rotated and spread apart, thus allowing a endotracheal tube to be inserted into the airway between the arcuate hooks. The arcuate hooks are then removed from the airway by moving the handles downward toward the patient's sternum and in turn levering the hooks out of the airway.

An object of the invention is to reduce the number of instruments required to perform surgical cricothyrotomy.

Another object of the invention is to provide a safe, simple and reliable procedure to perform surgical cricothyrotomy.

Yet another object of the invention is to provide a compact, highly portable and reliable instrument which can be used to perform surgical cricothyrotomy.

Further objects and advantages of the invention will be brought out in the following portions of the specification, wherein the detailed description is for the purpose of fully disclosing preferred embodiments of the invention without placing limitations thereon.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 6A through FIG. 6G diagrammatically shown a method of performing a cricothyrotomy in accordance with the present invention using the surgical instrument of FIG. 1 coupled to a scalpel.

DETAILED DESCRIPTION OF THE INVENTION

Referring more specifically to the drawings, for illustrative purposes the present invention is embodied in the apparatus generally shown in FIG. 1 through FIG. 5 and in the method of performing an emergency surgical cricothyrotomy generally shown in FIG. 6A through FIG. 6G. It will be appreciated that the apparatus may vary as to configuration and as to details of the parts, and that the method of may vary as to the steps and their sequence without departing from the basic concepts as disclosed herein.

Figure 1:
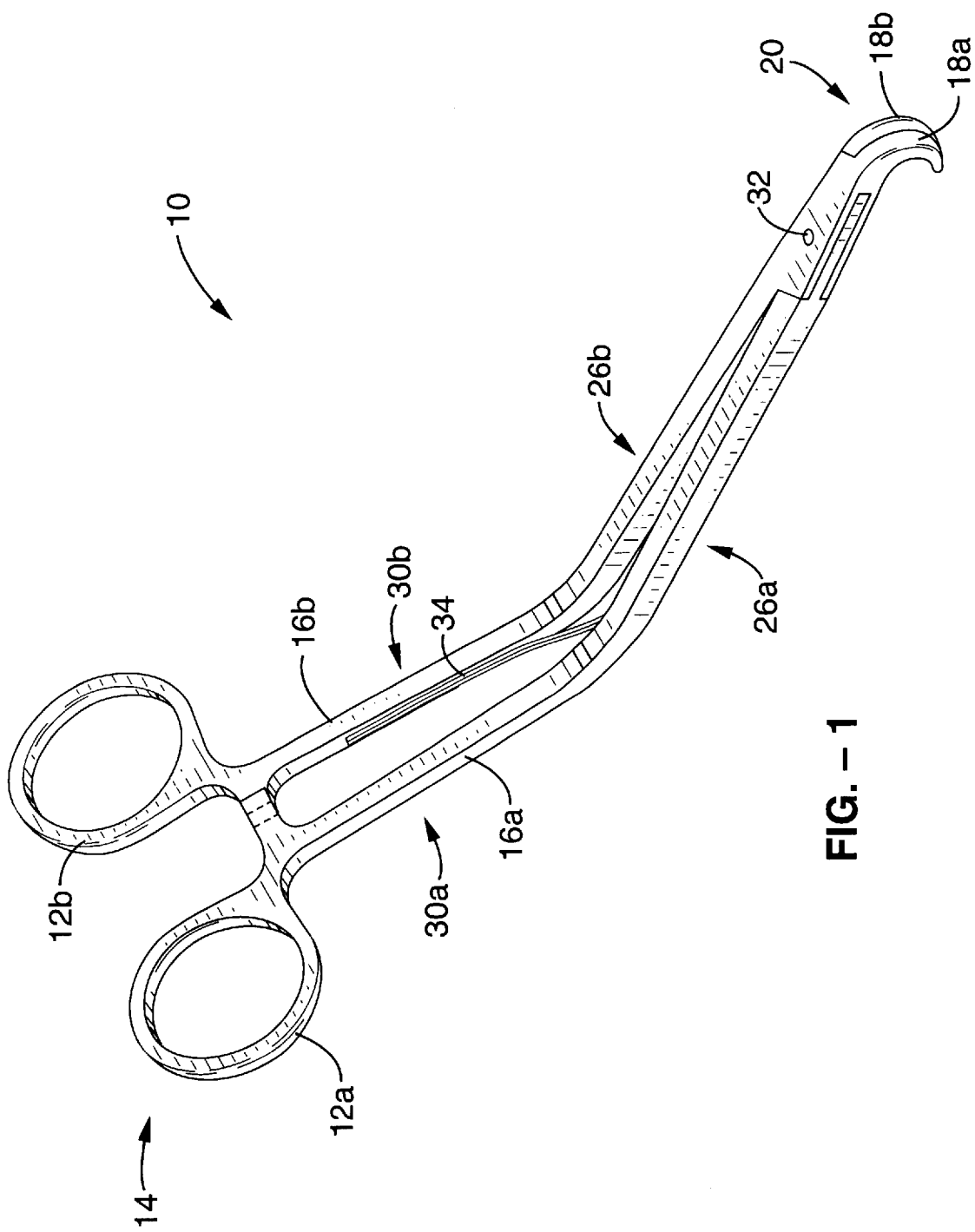
FIG. 1 is a perspective view of a surgical instrument in accordance with the present invention.
Figure 2:
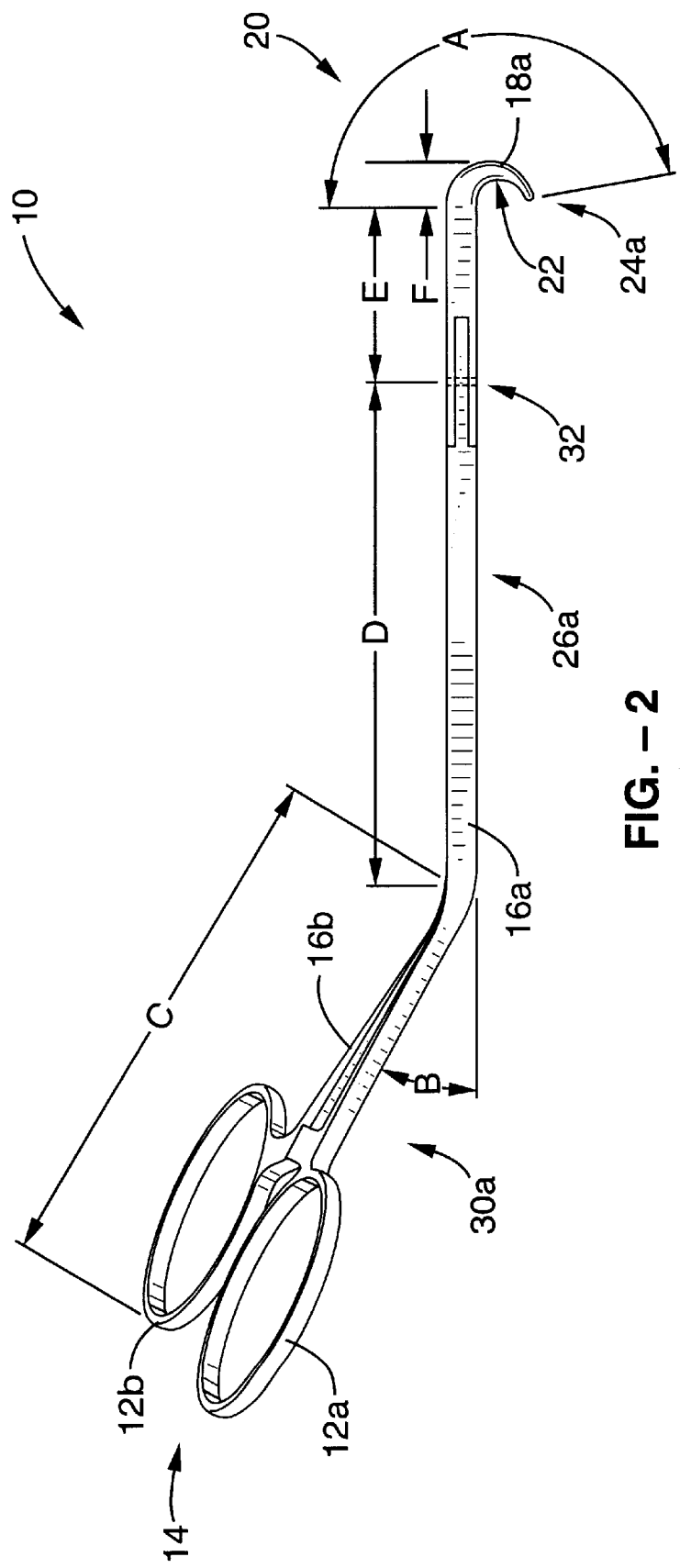
FIG. 2 is a side elevation view of the surgical instrument shown in FIG. 1.
Figure 3:
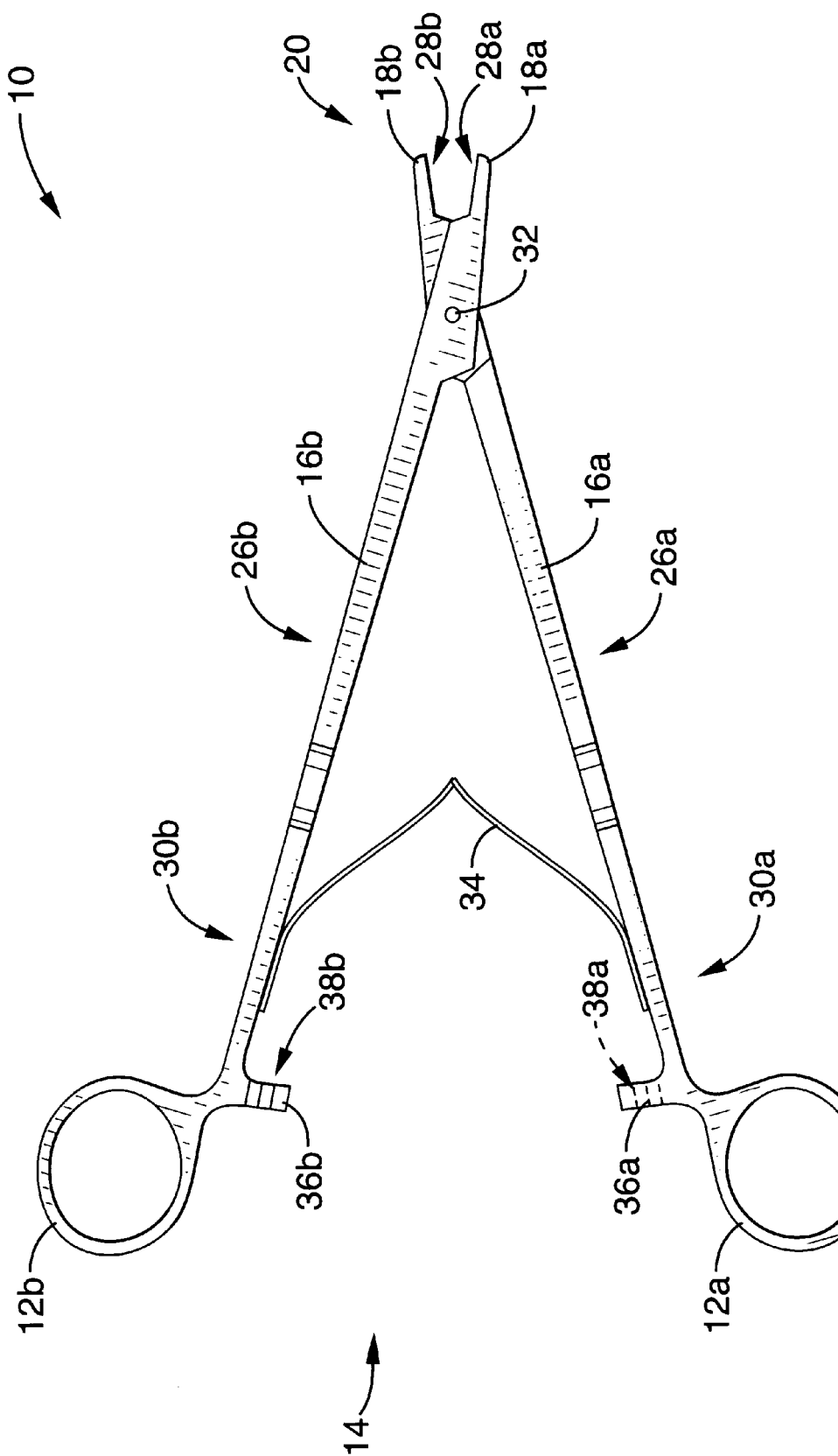
FIG. 3 is a top plan view of the surgical instrument shown in FIG. 1.

Referring first to FIG. 1 through FIG. 3, a surgical instrument 10 in accordance with the present invention is generally shown. The instrument includes a pair of adjacent handles 12a, 12b at its proximal end 14, with a pair of corresponding elongated shafts 16a, 16b extending therefrom and terminating at hooks 18a, 18b, respectively, at the distal end 20 to form an arcuate nose of the instrument. Hooks 18a, 18b are arcuate in shape and have a small radius of curvature 22, not exceeding an angle of approximately ninety degrees similar to a conventional tracheal hook. Referring more particularly to FIG. 2, hooks 18a, 18b terminate at tips 24a, 24b (not shown) which sweep an arc "A" at approximately one hundred and seventy degrees relative to the longitudinal axis of distal segments 26a, 26b of shafts 16a, 16b. Hooks 18a, 18b have opposing inner surfaces 28a, 28b that are aligned in generally parallel engagement when hooks 18a, 18b are in a closed position so as to provide a secure gripping surface.

As can be seen in FIG. 2, the proximal segments 30a, 30b of shafts 16a, 16b to which handles 12a, 12b are attached are offset relative to the longitudinal axis of the distal portions 26a, 26b of shafts 16a, 16b as shown. The angle of offset "B" is preferably approximately thirty degrees in an opposite direction to the direction in which tips 24a, 24b curve away from the distal segments 26a, 26b of shafts 16a, 16b. This provides for easy removal of hooks 18a, 18b from the cricothyroid membrane and subcutaneous tissues during a cricothyrotomy as discussed more fully below, whereby the user merely has to push handles 12a, 12 downward towards the patient's chest to lever out hooks 18a, 18b. This is a significant feature of the invention as it provides for performance of a cricothyrotomy quickly and efficiently without handles 12a, 12b being obstructed by the patient's sternum when the instrument is being removed.

Referring to FIG. 3, shafts 16a, 16b are pivotally coupled crosswise by a pin 32 to provide a scissor action of the shafts in response to movement of handles 12a, 12b. Shafts 16a, 16b can be captively held in place by pin 32 similar to a conventional hemostat, or the shafts can be detachable to allow the instrument to be disassembled into two sections and used independent as, for example, tracheal hooks if desired. In the preferred embodiment of the invention, hooks 18a, 18b are closed by drawing handles 12a, 12b together as in a conventional hemostat, and a normally expanded spring 34 is positioned between shafts 16a, 16b to hold handles 12a, 12b and hooks 18a, 18b in a normally open position. Alternatively, spring 34 could be replaced with a spring that is normally compressed so as to maintain handles 12a, 12b and hooks 18a, 18b in a normally closed position. It is also contemplated that, instead of coupling 16a, 16b a crosswise manner as shown, the shafts could be placed adjacent to each other and coupled in a conventional adjacent manner such that squeezing handles 12a, 12b together would open hooks 18a, 18b rather than close them.

In the embodiment shown, handles 12a, 12b and hooks 18a, 18b can be locked in a closed position by means of a locking mechanism comprising a pair of opposing tabs 36a, 36b extending from the proximal portions 30a, 30b of shafts 16a, 16b. Tabs 36a, 36b have serrations 38a, 38b which allow the tabs to frictionally engage and "hold" on to each other when handles 12a, 12b are squeezed together. The locking mechanism is disengaged by squeezing handles 12a, 12b such that serrations 38a, 38b spread apart as in a conventional hemostat.

Referring again to FIG. 2, the dimensions of surgical instrument 10 can vary but it has been found that certain dimensions provide for compact storage, ease of use, and rapid deployment of a cricothyrotomy. Preferably the distance "C" between the proximal end of the instrument and the offset point 40 between the proximal and distal portions of shafts 16a, 16b is approximately 2.0 inches, the distance "D" between offset point 40 and pin 32 is approximately 2.75 inches, the distance "E" between pin 32 and the distal end of shafts 16a, 16b is 0.75 inches, and the distance "F" between the distal end of shafts 16a, 16b and the distal end of hooks 18a, 18b is approximately 0.25 inches. In addition, surgical instrument 10 is preferably constructed of standard materials for instruments of like nature used in the medical field, such as stainless steel or titanium.

Figure 4:
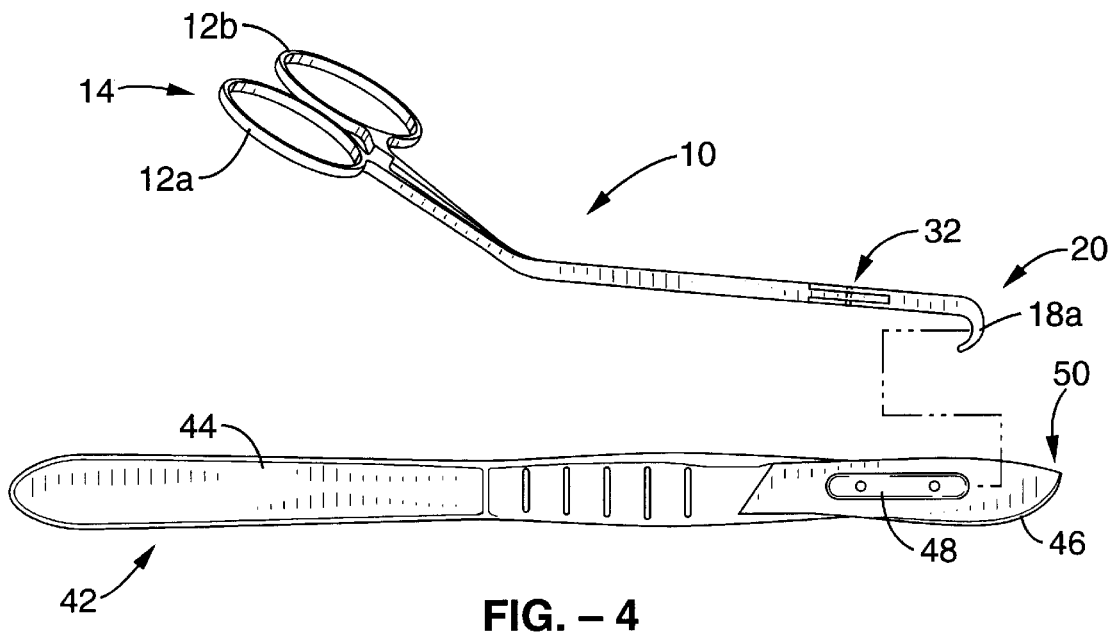
FIG. 4 is an exploded side elevation view showing the surgical instrument of FIG. 1 posited adjacent to a scalpel for coupling as a unitary instrument.
Figure 5:
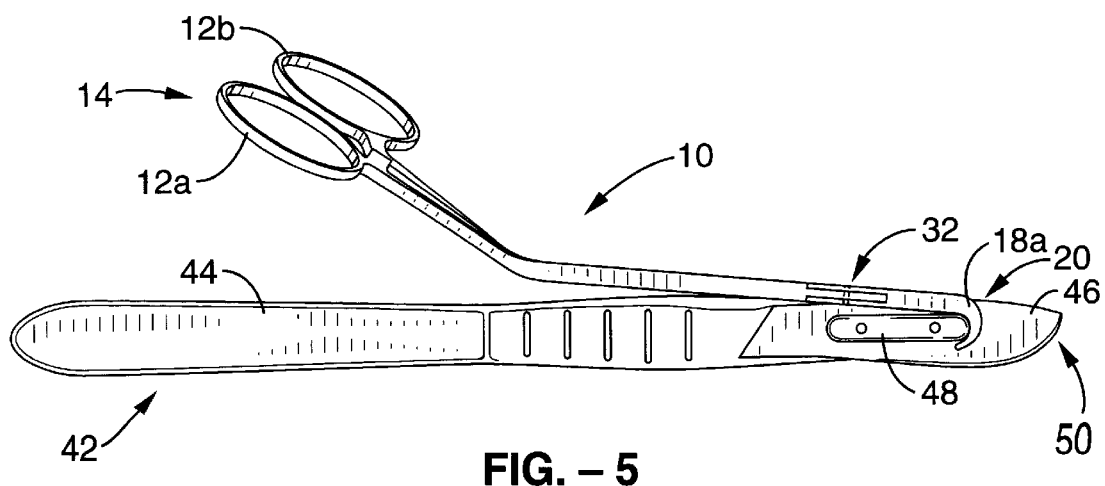
FIG. 5 is an assembled side elevation view showing the surgical instrument of FIG. 1 coupled to a scalpel as a unitary instrument.

Referring now to FIG. 4 and FIG. 5, the configuration of hooks 18a, 18b permits the apparatus to mate with and hold a scalpel or other surgical cutting instrument in a unitary fashion. In other words, the person performing a cricothyrotomy no longer must hold a scalpel in one hand, and a tracheal hook in the other hand. The present invention allows the procedure to be initiated with one hand as more fully described below, thus freeing the other hand for identifying the cricothyroid membrane and stabilizing the larynx.

Many commonly available scalpels 42, primarily those of a disposable type, comprise a handle 44 and a blade 46. The blade 46 typically includes a cutout portion (not shown) that fits over a hub 48 that protrudes from one side of the handle to secure the blade in place. In the present invention, the blade 46 of a scalpel 42 can be positioned between the inner surfaces 28a, 28b of hooks 18a, 18b. Then, when the blade 46 is positioned distal of hooks 18a, 18b, hub 48 will engage the inner arcuate surface of hook 18a or 18b, depending on the side of the scalpel that hub 48 is positioned. By "wrapping around" the hub 48, the hook will restrict longitudinal motion of the scalpel relative to the hooks. At the same time, by closing handles 12a, 12b, the blade 46 will be compressed by the inner surfaces 28a, 28b of hooks 18a, 18b and held in place. While hub 48 is shown as having an elongated shape, other shapes can be employed. Ideally, however, the radius of curvature and size of the hub will match that of inner arcuate surface of the hook which wraps around the hub for a secure fit.

Those skilled in the art will appreciate that, by placing a second hub on the other side of the scalpel, both hooks will abut a hub and a more secure engagement would result. It will further be appreciated that, by positioning the hubs relative to the distal end 50 of the blade 46, the distance by which blade 46 protrudes beyond the distal end 20 of the apparatus can be controlled. By limiting this distance, the depth to which blade 46 can cut will be limited since hooks 18a, 18b will abut the surface tissue and prevent blade 46 from cutting deeper than the distance by which blade 46 extends beyond hooks 18a, 18b.

Figure 6A:
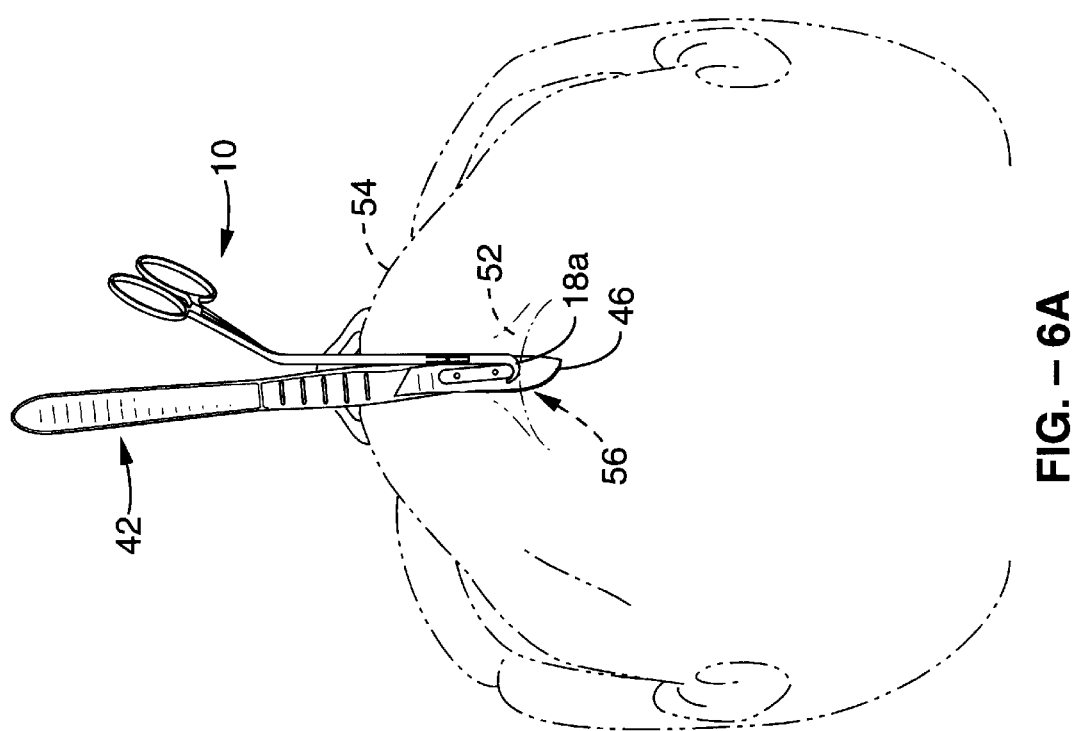

Referring now to FIG. 6A through FIG. 6G, an exemplary cricothyrotomy procedure in accordance with the present invention is diagrammatically shown. Referring first to FIG. 6A, the apparatus 10 and scalpel 42 are coupled together to form an unitary instrument. The apparatus 10 engages and holds scalpel 42 by clamping blade 46 between hooks 18a, 118 b, and the relative position of hooks 18a, 18b and the distal end of blade 46 determines the limit of the blade's incision depth. The apparatus 10 and scalpel 42 are then conjunctively used to make a lateral incision in the skin and cricothyroid membrane 52 of the patient 54. Referring to FIG. 6B, once access to the airway 56 is achieved, hooks 18a, 18b are gently advanced into the airway 56 while, at the same time, scalpel 42 is removed. Then, as shown in FIG. 6C, the apparatus 10 is rotated caudad so that axial traction may be applied. Next, as shown in FIG. 6D, hooks 18a, 18b are spread apart, thus causing dilation of the membrane 52 and subcutaneous tissues. Once dilated, an endotracheal tube 58 is placed into the airway 56 between the open hooks 18a, 18b as shown in FIG. 6E. Finally, handles 12a, 12b are pushed downward toward the patient's sternum 60 as shown in FIG. 6F and FIG. 6G to lever hooks 18a, 18b out of the airway 56. Note that with the use of this apparatus, the need for a tracheal hook to apply traction and a hemostat to dilate the membrane and tissue is effectively eliminated.

Accordingly, it can be seen that the present invention reduce the number of instruments required to perform surgical cricothyrotomy, and provides for a safe, simple and reliable procedure to perform surgical cricothyrotomy using a compact, highly portable and reliable surgical instrument. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. An apparatus for establishing a surgical airway in a patient comprising:

(a) a pair of pivotally coupled shafts, said shafts having first and second ends;

(b) a pair of handles extending from said first ends of said shafts;

(c) a pair of opposing arcuate hooks extending from said second ends of said shafts, said hooks moveable by said handles between an open and closed position; and (d) a scalpel, said scalpel having a first side and a second side, said scalpel including a hub protruding outwardly from a side of said scalpel, said sides of said scalpel positioned between said hooks; and (e) means associated with at least one of said hooks for engaging said hub.

2. An apparatus as recited in claim 1, wherein said handles are angularly offset from said shafts in a direction opposite to a direction of curvature of said hooks.

3. An apparatus as recited in claim 1, wherein said shafts have first and second segments, wherein each said segment of said shafts having a longitudinal axis, wherein said handles extend from said first segments of said shafts, wherein said hooks extend from said second segments of said shafts, wherein said hooks curve away from said second segments of said shafts in a first direction, wherein the longitudinal axes of said first segments of said shafts are angularly offset from the longitudinal axes of said second segments of said shafts in a second direction opposite said direction of curvature of said hooks.

4. An apparatus as recited in claim 1, further comprising means for biasing said hooks in said open position.

5. An apparatus as recited in claim 1, further comprising means for locking said hooks in said closed position.

6. An apparatus as recited in claim 1, wherein said shafts are detachable.

7. An apparatus for establishing a surgical airway in a patient comprising:

(a) a pair of pivotally coupled shafts, said shafts having first and second ends;

(b) a pair of handles extending from said first ends of said shafts;

(c) a pair of opposing arcuate hooks extending from said second ends of said shafts;

(d) said handles angularly offset from said shafts in a direction opposite to a direction of curvature of said hooks, said hooks moveable by said handles between an open and closed position;

(e) a surgical blade, said surgical blade having a first side and a second side, said surgical blade including a hub protruding outwardly from a side of said surgical blade, said sides of said surgical blade positioned between said hooks; and (f) means associated with at least one of said hooks for engaging said hub.

8. An apparatus as recited in claim 7, further comprising means for biasing said hooks in said open position.

9. An apparatus as recited in claim 7, further comprising means for locking said hooks in said closed position.

10. An apparatus as recited in claim 7, wherein said shafts are detachable.

11. An apparatus for establishing a surgical airway comprising:

(a) a pair of pivotally coupled shafts, said shafts having first and second segments, wherein each segment of said shafts has a longitudinal axis;

(b) a pair of handles;

(c) a pair of opposing arcuate hooks extending from said second segment, wherein said hooks extend from said second segment of said shafts, wherein said handles extend from said first segments of said shafts, wherein said hooks curve away from said second segments of said shafts in a first direction, wherein the longitudinal axis of said first segments of said shafts are angularly offset from the longitudinal axis of said second segments of said shafts in a second direction opposite said direction of curvature of said hooks, wherein said hooks are moveable by said handles between an open and closed position;

(d) a surgical blade, said surgical blade having a first side and a second side, said surgical blade including a hub protruding outwardly from a side of said surgical blade, said sides of said surgical blade positioned between said hooks; and (e) means associated with at least one of said hooks for engaging said hub.

12. An apparatus as recited in claim 11, further comprising means for biasing said hooks in said open position.

13. An apparatus as recited in claim 11, further comprising means for locking said hooks in said closed position.

14. An apparatus as recited in claim 11, wherein said shafts are detachable.

* * * * *